United States Patent
Drake et al.

(10) Patent No.: US 7,918,813 B2
(45) Date of Patent: Apr. 5, 2011

(54) FLEXIBLY ADJUSTABLE DORSAL SPLINT (75) Inventors: Jesse Drake, Clinton, MA (US);
Richard J. Clement, Sudbury, MA (US); Julian H. Cherubini, Boston, MA (US)

(73) Assignee: AliMed, Inc., Dedham, MA (US)

( * ) Notice: Subject to any disclaimer, the term of this patent is extended or adjusted under 35 U.S.C. 154(b) by 337 days.

(21) Appl. No.: 12/074,686

(22) Filed: Mar. 5, 2008

(65) Prior Publication Data
US 2009/0227928 A1 Sep. 10, 2009

(51) Int. Cl.
*A61F 5/00* (2006.01)
*A61F 5/37* (2006.01)
*A61F 13/06* (2006.01)

(52) U.S. Cl. ............... 602/28; 602/5; 128/882; 128/892

(58) Field of Classification Search ............. 602/27, 602/28, 2, 5, 6, 60, 61, 62, 65, 29; 128/888, 128/882, 892; 36/154, 140, 145, 155, 160, 36/161, 162
See application file for complete search history.

(56) References Cited

U.S. PATENT DOCUMENTS

| | | | |
|---|---|---|---|
| 4,100,918 A * | 7/1978 | Glancy | 602/16 |
| 5,086,761 A * | 2/1992 | Ingram | 602/26 |
| 5,399,155 A | 3/1995 | Strassburg et al. | |
| 5,772,619 A * | 6/1998 | Corbett | 602/16 |
| 5,776,090 A | 7/1998 | Bergmann et al. | |
| 5,799,659 A | 9/1998 | Stano | |
| 5,897,520 A | 4/1999 | Gerig | |
| 6,019,741 A | 2/2000 | Prieskorn | |
| 6,126,625 A * | 10/2000 | Lundberg | 602/27 |
| 6,267,742 B1 * | 7/2001 | Krivosha et al. | 602/28 |
| 6,361,514 B1 | 3/2002 | Brown et al. | |
| 6,699,209 B2 | 3/2004 | Turtzo | |
| 6,991,613 B2 | 1/2006 | Sensabaugh | |
| 7,182,743 B2 | 2/2007 | Slautterback et al. | |
| 2008/0004558 A1 * | 1/2008 | Outred et al. | 602/28 |

* cited by examiner

*Primary Examiner* — Patricia M Bianco
*Assistant Examiner* — Ophelia Hawthorne
(74) *Attorney, Agent, or Firm* — Wolf, Greenfield & Sacks, P.C.

(57) ABSTRACT

An apparatus and method for treating plantar fasciitis are disclosed. In one embodiment of the apparatus, a dorsal splint device includes an upper portion and a foot portion which are pivotally connected to one another. A strap allows attachment of the upper portion to a suitable portion of the leg, such as the calf. A tensioning element, such as a shock cord, urges the foot portion and the upper portion toward one another. The tension provided by the tensioning element may be adjusted by adjusting the length of the tensioning element. In the method of the present invention, the tensioning element may be first unhooked to allow pivoting of the foot portion with respect to the upper portion so that the device may be attached to a user. The tensioning element is then hooked to the device at the appropriate position to provide the desired tension urging the foot portion toward the upper portion.

25 Claims, 6 Drawing Sheets

FLEXIBLY ADJUSTABLE DORSAL SPLINT

BACKGROUND OF INVENTION

1. Field of Invention

The present invention relates to articles and methods for use in treating plantar fasciitis.

2. Discussion of Related Art

The plantar fascia is a thick connective tissue support for the arch of the foot, running from the calcaneous bone of the heel to the metatarsals at the front part of the foot. Excessive wear in the plantar fascia commonly due to long periods of weight bearing usually results in a sharply painful inflammatory condition, typically felt on the underside of the heel, known as plantar fasciitis. Sports activity, weight gain, walking on hard surfaces, using shoes with little or no arch support, and inactivity are all associated with the condition. Plantar fasciitis usually develops gradually, but it can come on suddenly and severely. Although it has been shown to affect both feet, it more often occurs in only one foot at a time. Plantar fasciitis is also commonly associated with a sharp pain that is typically worse after long periods of inactivity (e.g., sleeping or sitting) and can be mitigated by stretching of the lower leg connective and muscle tissues. Physical therapy exercises commonly performed to treat the condition include stretching the plantar fascia and Achilles tendon and strengthening lower leg muscles, which serve to stabilize the ankle and heel regions. In addition, patients should be encouraged to lessen activities which place more pressure on the balls of the feet. Night splints can be used to keep the foot in a dorsi-flexed position to improve calf muscle flexibility and decrease pain. Examples of night splints used for such purposes include those shown in U.S. Pat. Nos. 7,182,743; 6,991,613; 6,361,514; 5,897,520; 5,799,659; 6,019,741; 6,699,209; 6,267,742; 5,776,090; and 5,399,155. More aggressive treatments such as extracorporeal shock therapy or surgery are used for chronic plantar fasciitis that has not responded to more conservative approaches, but are only recommended as a last resort for extreme occurrences of the condition.

SUMMARY OF INVENTION

In one aspect, a therapeutic device is provided. In one embodiment, the therapeutic device includes an upper portion constructed to be disposed adjacent to a bone of a lower leg, and a foot portion constructed to be disposed adjacent to a cuneiform bone of a foot. The foot portion may be pivotally connected to the upper portion at a pivot point. A lower leg strap may be connected to the upper portion and constructed to be wrapped about the lower leg. A foot strap may be connected to the foot portion and constructed to be wrapped about a foot. Lastly, an elastic tensioning element typically extends between spaced, confronting locations on the upper portion and the foot portion, the locations being spaced from the pivot point.

In another illustrative embodiment, the therapeutic device includes an upper portion and a foot portion pivotally connected to the upper portion at a pivot point. A lower leg strap may be connected to the upper portion and a foot strap may be connected to the foot portion. An elastic tensioning element comprises a single shock cord and typically extends between spaced, confronting locations on the upper portion and the foot portion, the locations being spaced from the pivot point.

In another aspect, a method for treating plantar fasciitis is provided. The method includes providing a splint having an upper portion and a foot portion, in which the upper portion and foot portion are pivotally disposed with respect to one another at a pivot point. The method may also comprise securing the upper portion of the splint to a lower leg adjacent a bone and securing the foot portion to an upper surface of a foot adjacent a cuneiform bone. The method further includes urging the foot portion and upper portion together with an elastic tensioning element extending between the foot portion and the upper portion, and providing a desired tension by selecting the point on the tensioning element where it is attached to either the upper or foot portions.

Various embodiments of the present invention provide certain advantages. Not all embodiments of the invention share the same advantages and those that do may not share them under all circumstances.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. Further features and advantages of the present invention, as well as the structure of various embodiments of the present invention are described in detail below with reference to the accompanying drawings, in which.

DETAILED DESCRIPTION

Aspects of the invention are not limited in application to the details of construction and the arrangement of components set forth in the following description or illustrated in the drawings. Aspects of the invention are capable of other embodiments and of being practiced or carried out in various ways. In addition, aspects of the invention may be used alone and/or in any suitable combination with any other aspect(s) of the invention. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Figure 1:
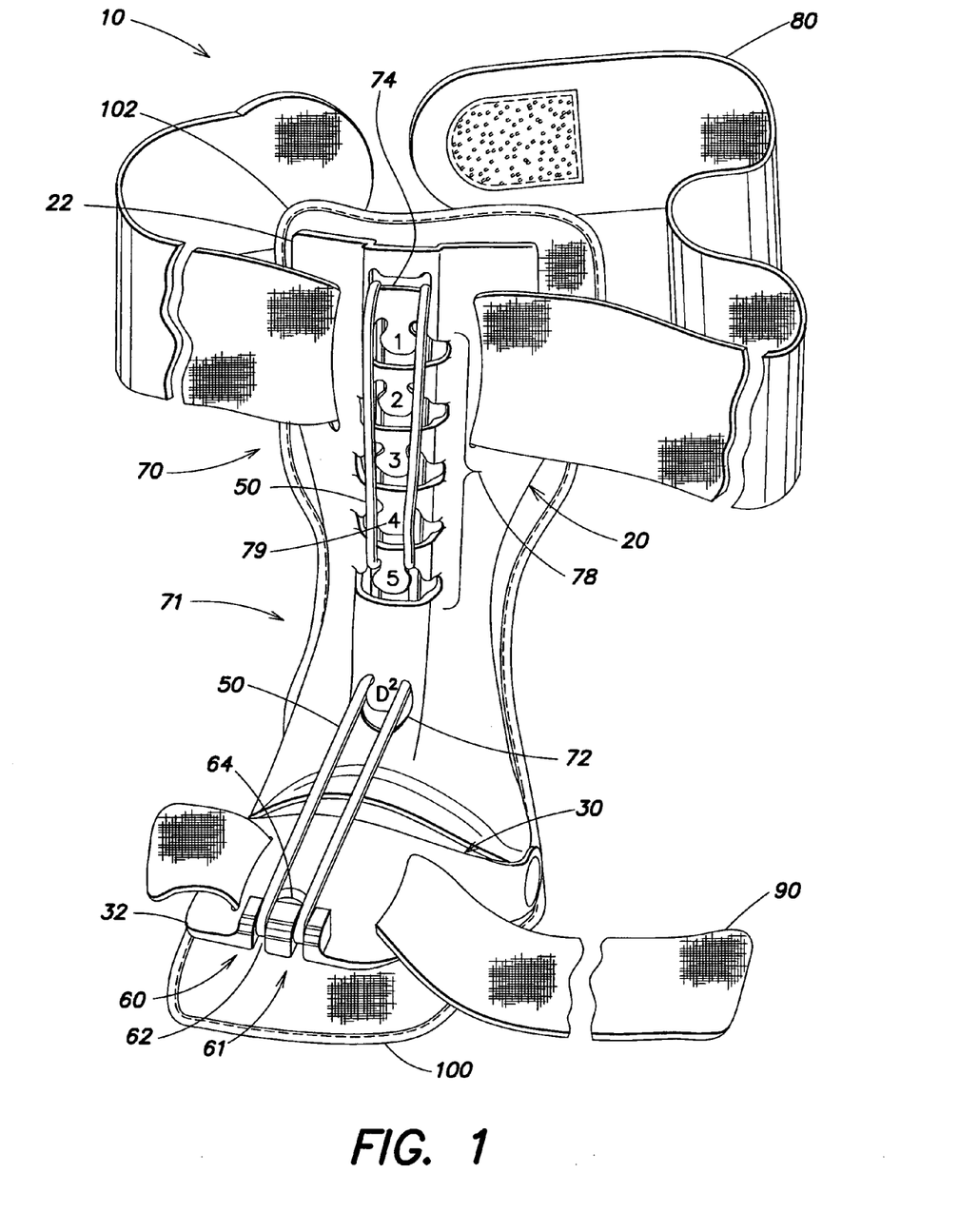
FIG. 1 is a perspective view of a dorsal splint device of this invention for treating plantar fasciitis according to embodiments of the invention.
Figure 2:
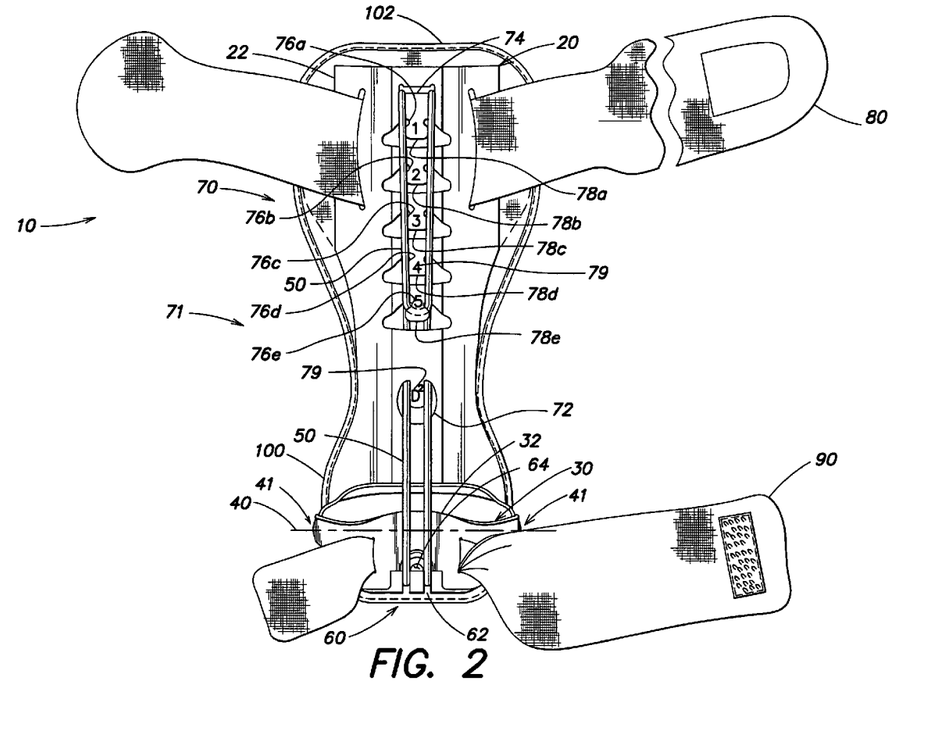
FIG. 2 is a front view of the dorsal splint device of FIG. 1.

The present invention relates to an apparatus and method for treating plantar fasciitis by adjustably stretching the plantar fascia and Achilles tendon using a dorsal splint device 10. In one embodiment, as shown in FIGS. 1 and 2, device 10 includes an upper portion 20 and a foot portion 30. At least one flexibly adjustable tensioning element 50 extends between said upper portion 20 and said foot portion 30. The tensioning element 50 typically is anchored at confronting points of the upper portion 20 and the foot portion 30. Tensioning element 50 may be used to urge or pull upper portion 20 and foot portion 30 towards one another.

It should be appreciated that the device 10 may be used in a number of effective ways in treating plantar fasciitis. In one embodiment, the tensioning element 50 may be used to impart a significant amount of stretching tension to the plantar fascia and Achilles' tendon of the user by urging the upper portion 20 and foot portion 30 together. In another embodiment, the tensioning element 50 may be used to impart only a slight amount of stretching tension to the plantar fascia and Achilles' tendon of the user by maintaining the orientation of the upper portion 20 relative to the foot portion 30 of the device 10 such that the foot 300 (FIG. 3) remains in a relatively comfortable dorsi-flexed position.

Figure 3:
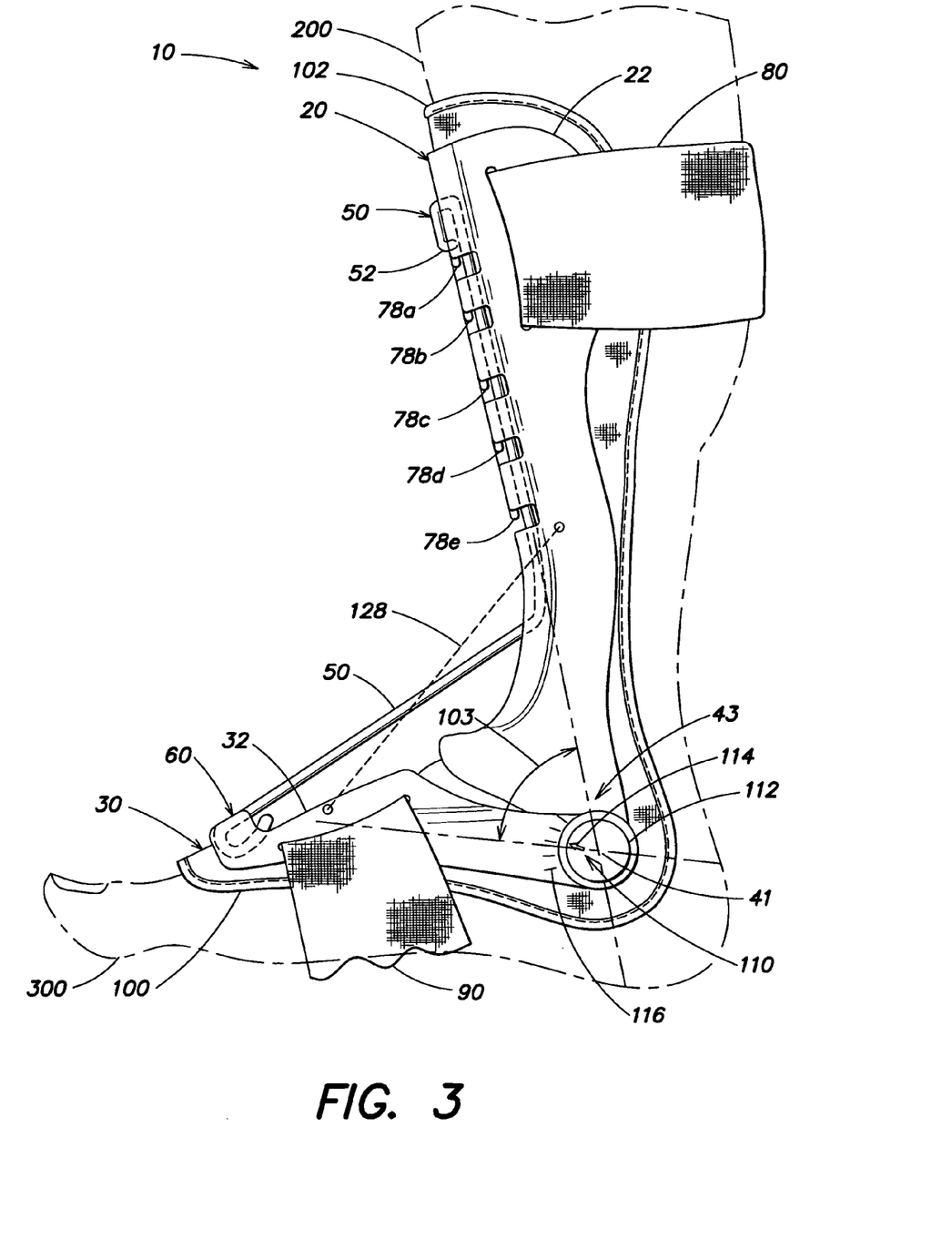
FIG. 3 is a side view of the dorsal splint device of FIG. 1 illustrating one angled configuration.
Figure 4:
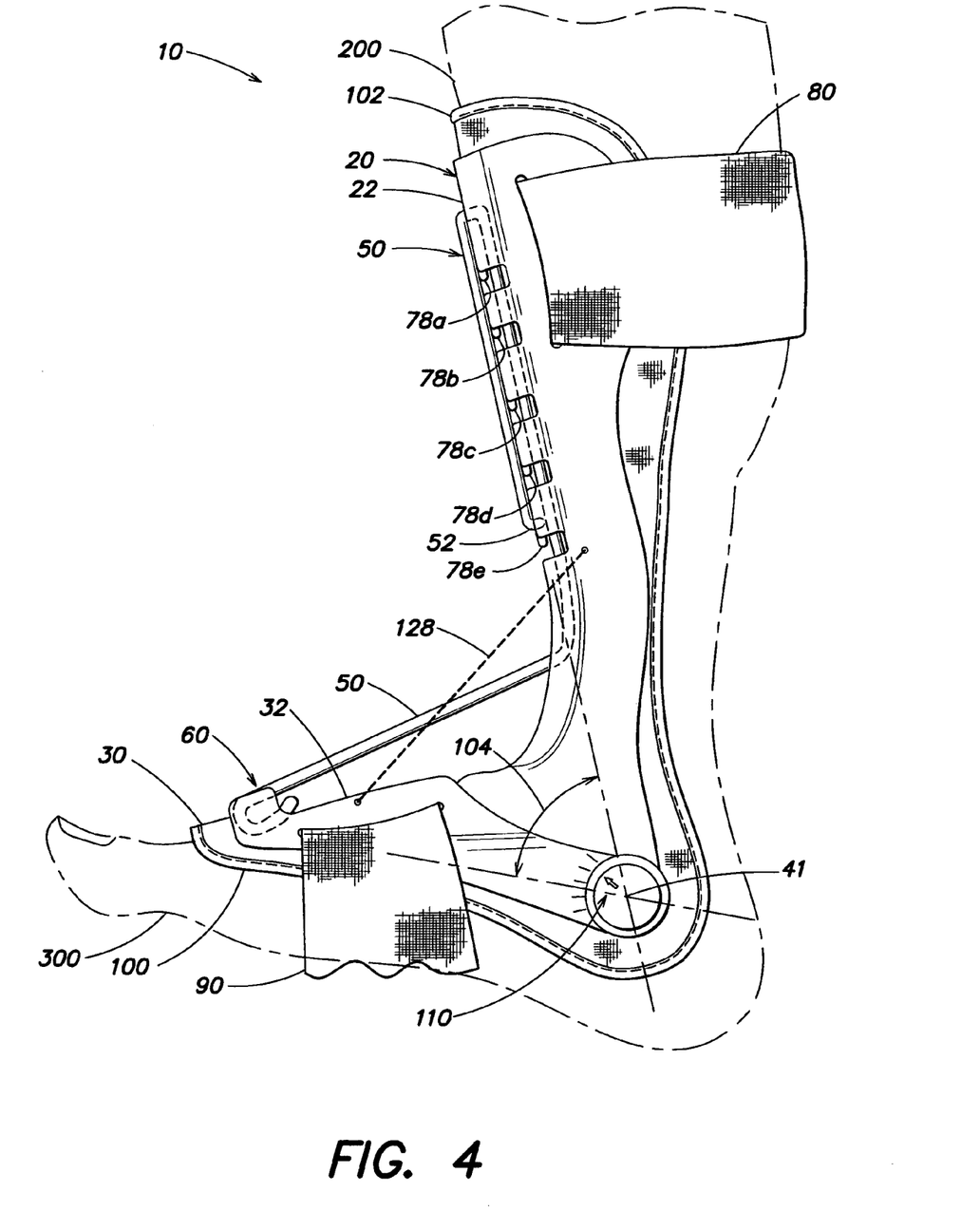
FIG. 4 is a side view of the dorsal splint device of FIG. 1 illustrating another angled configuration.

As shown in FIGS. 3 and 4, when device 10 is worn, typically portions 20 and 30 are positioned such that they may be comfortably and adjustably strapped on to a leg 200 and foot 300, respectively, of a user. In one embodiment, when worn, the upper portion 20 is located on the dorsal side of the leg 200 adjacent to a shin bone of the user. In this embodiment, the foot portion 30 is typically located on the dorsal side of the foot 300 adjacent to the cuneiform bones of the user. In this configuration, tensioning element 50 may extend between confronting faces of upper portion 20 and foot portion 30. Tensioning element 50 then may also be pulled and oriented in a manner so as to adjust the amount of stretching resistance between portions 20 and 30.

Foot portion 30 may include an outer shell 32, a liner 100 and a foot strap 90. Upper portion 20 may include an outer shell 22, a liner 102 and a calf strap 80. In one embodiment, shells 22 and 32 may be relatively rigid. It should be appreciated that the shells 22 and 32 need not be completely rigid, but should be strong enough to provide a suitable attachment for tensioning element 50.

In one embodiment, the upper portion 20 and foot portion 30 are formed of a thermoplastic material processed via a number of techniques, including injection molding or extrusion. Typical thermoplastic materials that are used include polystyrene, polyethylene, acrylic, polypropylene, polyester, polyamide, polyvinyl chloride, and/or phenol formaldehyde. It should be appreciated that the upper and foot portions may be manufactured out of a wide variety of other suitable materials, for example, including metal, ceramic, wood, plastic, or any other desired material.

To secure upper portion 20 to the leg 200 of a user, calf strap 80 may be flexibly wrapped around an appropriate portion of leg 200, such as the calf. Similarly, to secure foot portion 30 to the foot 300 of a user, foot strap 90 may be flexibly wrapped around an appropriate portion of the foot 300. Calf strap 80 and foot strap 90 are typically made out of, but are not limited to, any suitably flexible material. For example, calf strap 80 and foot strap 90 may be formed of a suitable fabric or plastic which may or may not be elastic. In one embodiment, hook and loop fasteners located at the end portion of the calf strap 80 and the foot strap 90 are used to adjustably secure the device 10 to the user. It should be appreciated that any other suitable approach may also be used to secure the device to the user such as through tying, buckling, fastening, buttoning, wrapping, or hooking, for example. Liner 102 may be disposed between shell 22 and leg 200 for comfort when the device is worn. Liner 100 may be disposed between shell 32 and foot 300 for comfort. In this regard, liners 100 and 102 may or may not be continuous. While a liner 100 or 102, indeed, may be a useful accessory, it should be appreciated that in different aspects of the present invention, a liner is not necessarily present. On the other hand, it should also be appreciated that several liners or layers of liners may be incorporated in the device for increased comfort.

As shown in FIG. 2, upper portion 20 may be connected to foot portion 30 along a pivot axis 40. Upper portion 20 and foot portion 30 may be connected at two separate pivot points 41 along pivot axis 40. This arrangement allows relative pivotal motion between foot portion 30 and upper portion 20 about axis 40. Each point 41 may include a dowel, a pin, rivet, hinge, or any suitable connecting device that allows pivotal or rotatable motion to occur about point 41. The device is not limited to two separate pivot points, but could incorporate a single pivot point 41. Alternatively, the pivot axis 40 may also include more than two pivot points in the form of a joint that articulates in more complex, yet flexible aspects. Furthermore, a combination of a number of pivot axes and pivot points may also be integrated into the device, allowing for adaptable motion in a variety of users. In this manner, there may be several articulation points that will allow the device 10 to be suitably mounted onto the user. In addition, a lock 43 (FIG. 3) may be provided to fix the angular orientation of upper portion 20 with respect to foot portion 30, once the apt articulation orientation is chosen. Lock 43 may be any suitable, known locking or fastening device, such as a rotation stop mechanism, button stop, and/or ratchet stop mechanism.

Figure 5:
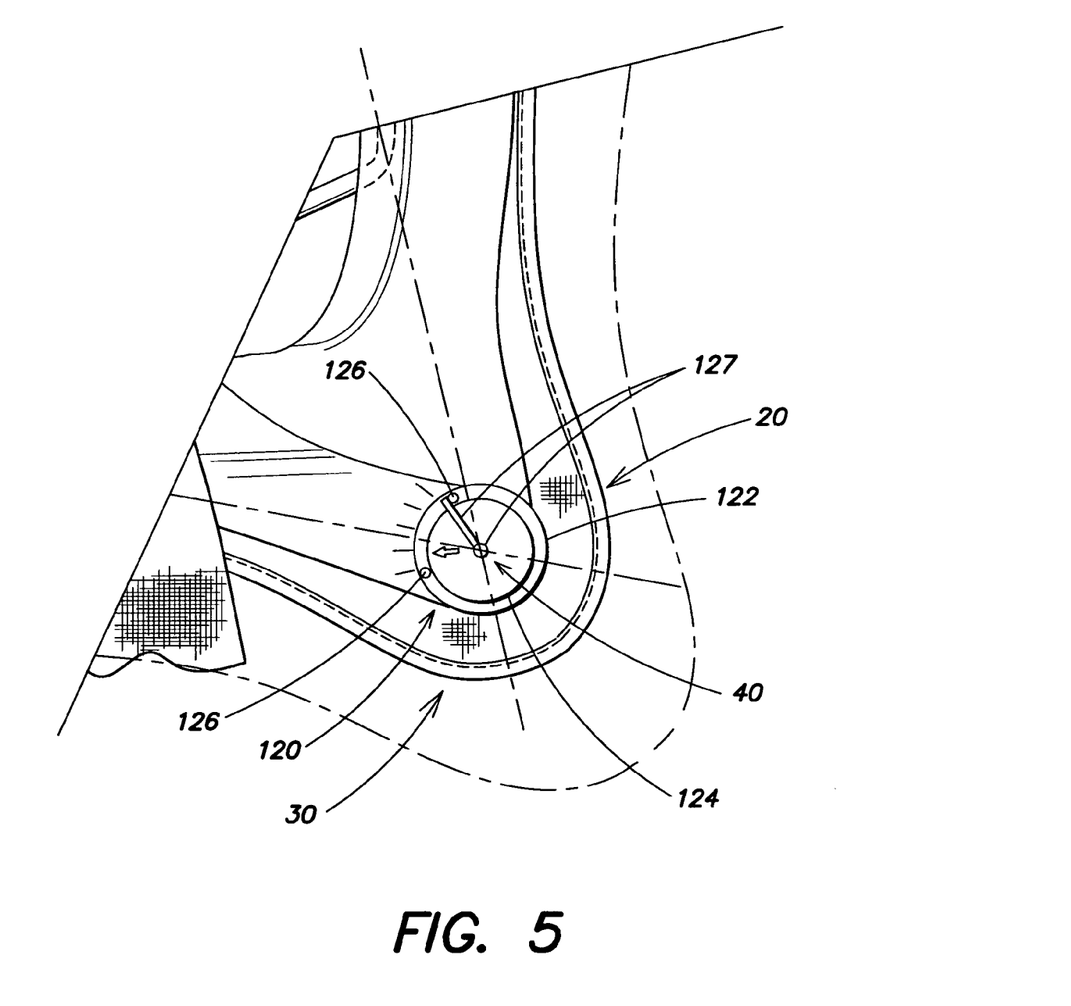
FIG. 5 is a partial side view of the dorsal splint device of this invention showing one embodiment of a stop.

In another aspect of the present invention, a stop may be provided to limit pivotal motion of upper portion 20 with respect to foot portion 30 about pivot axis 40 to thereby limit the maximum and/or minimum angle formed between portions 20 and 30. In one embodiment, as shown in FIG. 5, a mechanical stop 120 may be disposed at one or both of pivot points 41. Mechanical stop 120 may include two portions which are movable with respect to one another. In the exemplary embodiment shown in FIG. 5, an interior disc 124 may be surrounded by a second, annular disc 122. Disc 124 may be coupled to one of portions 20 or 30, while disc 122 may be coupled to the other of portions 20 and 30. Typically, discs 122 and 124 rotate with respect to one another about pivot axis 40. In this example, arm 127 is affixed to and rotates with disc 124 about pivot axis 40. Disc 122 includes at least one stop 126, and may include two stops 126. One of stops 126 may limit the maximum angle that portion 20 may form with respect to portion 30, while the other stop 126 may limit the minimum angle that portion 20 forms with respect to portion 30.

Figure 6:
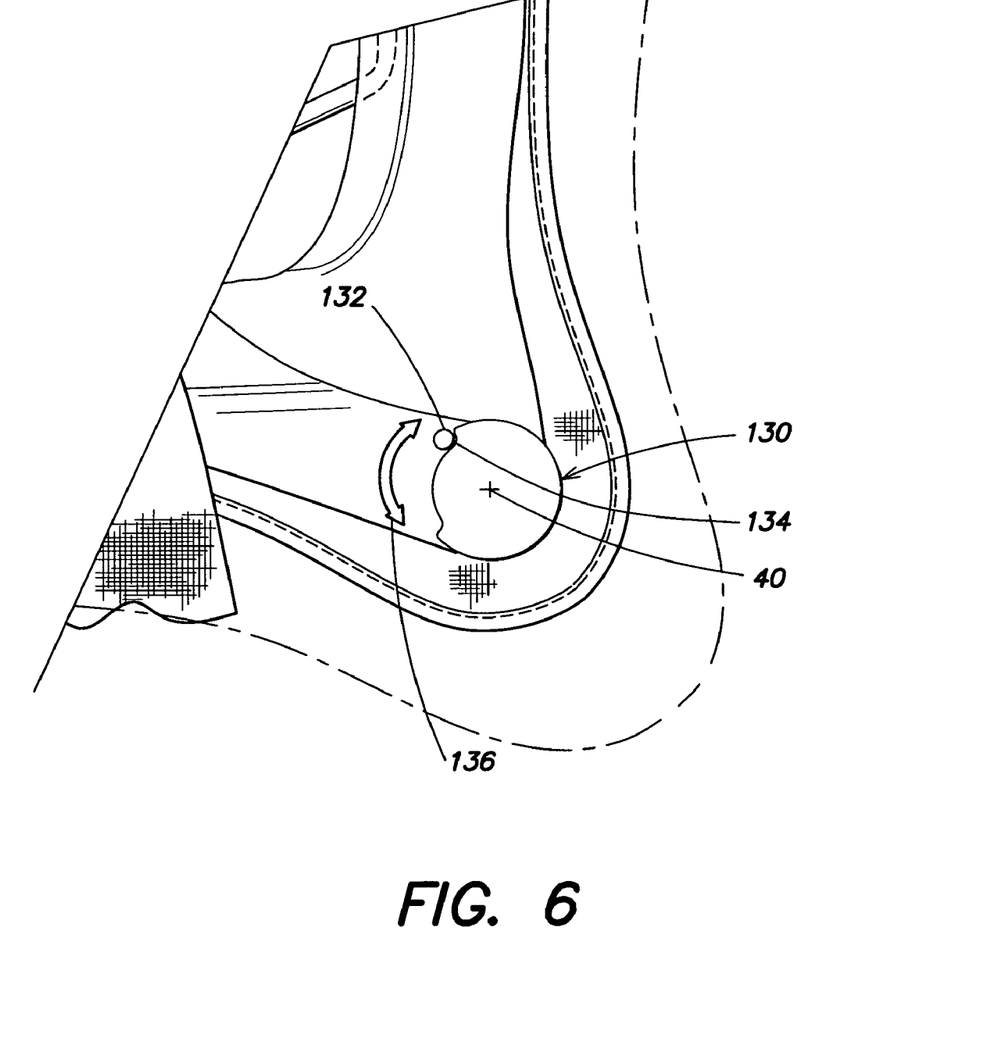
FIG. 6 is a partial side view of the dorsal splint device of this invention showing another embodiment of a stop.

In another aspect of the present invention, a combination of a cam 130 and a lug 132 may be disposed at one or both of pivot points 41. In one embodiment, as shown in FIG. 6, a cam 130 is affixed to upper portion 20 and may be pivoted in the direction shown by arrow 136 about axis 40. Cam 130 may include a cutout 134 that allows a lug 132 to travel therein. Lug 132 may be affixed to foot portion 30. Rotation of the upper portion 20 relative to the foot portion 30 is limited by the shoulders at the ends of cutout 134. Lug 132 may be removable if a greater range of motion is desired. While in one embodiment, cam 130 may rotate along with the upper portion 20 about pivot axis 40 and lug 132 may rotate along with foot portion 30, in other embodiments, cam 130 may rotate along with the foot portion 30, and lug 132 may rotate with the upper portion 20. In further embodiments, the cam 130 may be rotated and fixed in various positions so that the angle that upper portion 20 makes with foot portion 30 may be suitably adjusted.

In another embodiment, a non-elastic strap, rope or other flexible member may be provided extending from a point on portion 30 to another point on portion 20 as illustrated in phantom by reference numeral 128 in FIG. 3. Such a strap 128 serves to limit the maximum angle that portion 20 may form with respect to portion 30 when pivoting about pivot axis 40. It will be appreciated by one of ordinary skill in the art that other well-known stop mechanisms may be used to limit either the maximum angle that portion 20 forms with respect to portion 30, or the minimum angle that portion 20 forms with respect to portion 30.

Tensioning element 50 is located between the upper and foot portions and preferably is attached at anchor 70 on upper portion 20 and at anchor 60 on foot portion 30. Anchor 70 and anchor 60 both are typically spaced from pivot axis 40. Typically, anchors 60 and 70 are positioned on respective portions 30 and 20 such that anchors 60 and 70 face one another in a spaced, confronting relationship such that tensioning element 50 extends directly from anchor 60 to anchor 70 without interruption. In one aspect of the present invention, the tensioning element 50 is preferably elastic and is capable of sustaining large strains while maintaining high stress loads, and when unloaded, returning back to its original, resting configuration. In some embodiments, tensioning element 50 is an elastic shock cord, such as that commonly used for bungee sports activities. In other embodiments, tensioning element 50 may be any elastic device such as a spring, elastic band, or rubber cord. It should be appreciated that the device 10 is not limited to one tensioning element, but can incorporate more than one tensioning element or a combination of tensioning elements.

The location at which the tensioning element or elements 50 are anchored on foot portion 30 may vary. In one embodiment, anchor 60 for tensioning element 50 on foot portion 30 is disposed in a toe region 61, as shown in FIG. 1. In another embodiment, anchor 60 for tensioning element 50 on foot portion 30 is offset slightly to the right and/or the left of toe region 61 (not shown). In yet another embodiment, anchor 60 for tensioning element 50 on foot portion 30 is on either lateral side of the foot portion 30 (not shown). In a different embodiment, anchor 60 for tensioning element 50 on foot portion 30 may be on the bottom side of foot portion 30 (not shown). Indeed, it should be appreciated that there are many locations on foot portion 30 suitable for attachment of tensioning element 50, and multiple anchors 60 may be provided.

Similarly, the location or locations at which the tensioning element or elements 50 are anchored on upper portion 20 may also vary. In one embodiment, anchor 70 for tensioning element 50 on upper portion 20 is at the front of a lower shin region 71, as shown in FIG. 1. Anchor 70 for tensioning element 50 on upper portion 20 may also be at the front of a mid shin region (not shown). In another embodiment, anchor 70 for tensioning element 50 on upper portion 20 is at the front of an upper shin region (not shown). In a different embodiment, anchor 70 for tensioning element 50 on upper portion 20 may be on a lateral side of upper portion 20 (not shown). In still yet a different embodiment, anchor 70 for tensioning element 50 on upper portion 20 may be on a back side of upper portion 20 (not shown). Indeed, it should be appreciated that there are many different locations on upper portion 20 suitable for attachment of tensioning element 50, and multiple anchors 70 may be provided.

Anchor 60 may either provide for permanent attachment or temporary or adjustable attachment. In one embodiment, anchor 60 includes toe anchor grooves 62 and a toe anchor hook 64 through which tensioning element 50 may extend and be secured. In this embodiment, a loop of tensioning element 50 is guided through toe anchor grooves 62 and is wrapped around toe anchor hook 64. It should be understood that any suitable structure for securing tensioning element 50 could comprise toe anchor 60 and that the present embodiment is not limited in this manner. If a number of tensioning elements 50 are provided, a suitable number of toe anchors 60 may also be provided. For example, attachment sites may be provided in the form of grooves that are alternating or aligned adjacent to one another (not shown). In addition, a protrusion (not shown), separately attachable or previously connected, may also give rise to extra space for anchors 60. In another embodiment (not shown), ends of tensioning element 50 may be secured by a fastening mechanism such as a button, a buckle, a pin, a strap, or any suitable fastening device. In yet another embodiment, ends of tensioning element 50 may be secured by a device (not shown) that impedes movement of tensioning element 50. One example is a constricting sleeve or a clamping device that effectively secures the tensioning element in place. In another example tensioning element 50 is tied to itself in a knot and tensioning element 50 is slid into a slot that is small enough for the untied region of tensioning element 50 to fit through but too small for the knotted region of the tensioning element to fit through.

In one embodiment anchor 70 provides for adjustable attachment of element 50 and includes a proximal feed hole 72, an exit hole 74, grooves 76, and a hook 78. In this embodiment, element 50 passes through feed hole 72, out exit hole 74 and through grooves 76 to be secured at hook 78. For adjustability of the tensioning element 50, a plurality of spaced apart attachment points, or hooks 78 may be provided in anchor 70. FIG. 2 shows a plurality of grooves 76a, 76b, 76c, 76d, and 76e that correspond to a plurality of respective hooks 78a, 78b, 78c, 78d, and 78e. Indicia may be used to label hooks 78. For example, hooks may be numbered 1-5. It should be appreciated that when tensioning element 50 is hooked to hook 78a, as shown in FIG. 3, a greater unstretched length is created in tensioning element 50, allowing for a greater angle 103 to be formed between upper portion 20 and foot portion 30. In a similar way, when the tensioning element 50 is hooked to hook 78e, as shown in FIG. 4, a shorter unstretched length is created in tensioning element 50, reducing the angle 104 between upper portion 20 and foot portion 30. It should be understood that in other embodiments, as mentioned previously, tensioning device 50 could be attached to upper portion 20 in different ways. Examples include a pin attachment, or tying a knot in the tensioning element 50 so as to limit movement through an appropriately sized hole.

Because of the elastic nature of tensioning element 50, for a given angle between upper portion 20 and foot portion 30, the user may adjust the tension on element 50, by grasping the end of element 50, adjacent anchor 70, unhooking that end, and subsequently tensioning the element 50 and wrapping it around the desired hook 78 to produce the desired tension on element 50. Also, the tension on element 50 may be increased by increasing the angle 103 or 104 for a given unstretched length of element 50 by, for example, flexing the foot downwardly away from the leg about the ankle to stretch element 50. Similarly, the tension on element 50 may be decreased for a given unstretched length of element 50 by flexing the foot upwardly toward the leg about the ankle to reduce the angle 103 or 104. Moreover, the amount of tension between upper portion 20 and foot portion 30 depends in part on the resistance to bending provided by the foot. The amount of tension in the embodiment of FIG. 3 may be the same as, greater than or less than that found in FIG. 4 for element 50, depending on the natural angle between the leg and foot of a user.

In some embodiments, a range of motion indicator 110 (as shown in FIG. 3) is provided such as at pivot point 41, which can be helpful in tracking the progress of the user by showing the degree to which the foot is able to flex. Range of motion indicator 110 may record mechanically the progress through angle marks 116 thereon. In this embodiment, indicator 110 may include disc 112 which is fixedly secured to upper portion 20 and which has an indicator arrow 114 or the like displayed thereon. Disc 112 may pivot at its center about axis 40. As portions 20 and 30 pivot with respect to one another, arrow 114 pivots about pivot axis 40 with respect to angle marks 116. Range of motion indicator 110 may also record progress electronically through any suitable method. It should be appreciated that the progress of the user may be tracked in any other suitable manner, including observation of the range of motion.

In another aspect of this invention, a method of plantar fasciitis treatment and pain mitigation using device 10 is described. In this method, the foot 300 may be kept in a dorsi-flexed position to stretch the plantar fascia and the Achilles tendon. As the plantar fascia and/or Archilles tendon is stretched, the length of element 50 may be shortened to maintain the desired level of tension. Also, for any given foot angle, the tension on element 50 may be adjusted by selecting the desired hook 78. Some persons may prefer a greater or lesser tension for a given angle.

When mounting device 10 for treatment of plantar fasciitis, tensioning element 50 is, at first, unhooked from any of hooks 78 and the device 10 is opened such that the angle that foot portion 30 makes with upper portion 20 is equal to or greater than the natural angle between leg 200 and foot 300. Device 10 may then be easily attached to the user. The user will place the device on appropriate regions of leg 200 and foot 300 simultaneously or in whichever order is most desired. For the portion 20 or 30 that is most suitably attached first, the user will adjust the corresponding strap 80 or 90, wrap it comfortably but securely around the respective leg 200 or foot 300 and secure the strap 80 or 90 so that there is relatively little or no movement of device 10 with respect to the user's leg or foot. In a like manner, the user will proceed to the next portion 20 or 30 and similarly adjust the corresponding strap 80 or 90 by wrapping it about itself to secure the strap 80 or 90 so that there is relatively little or no movement of the device 10 with respect to the user's leg or foot. After both portions 20 and 30 are attached, appropriate small adjustments should be made for optimal comfort. In this aspect, the device 10 conforms to the overall structure of the leg and foot of the user.

Once device 10 is properly situated on the user through attachment of strap 80 and strap 90, end 52 of tensioning element 50 adjacent hooks 78 may be attached onto the appropriate hook 78 for the desired angle and tension. End 52 may be grasped and pulled to remove any slack and/or to increase the tension on tensioning element 50 to the desired level. The user then wraps end 52 around a selected hook 78 that maintains the level of tension and the angle between the foot and the leg desired by the user. Subsequently, foot portion 30 and upper portion 20 are urged toward one another by tension on element 50. Angle 103 or 104 generally will decrease over time. As it does so, the length and tension of element 50 may be progressively adjusted by securing element 50 at progressively lower hook locations 78a, 78b, 78c, 78d and 78e. In one embodiment, shown in FIG. 3, tensioning element 50 is hooked onto proximal hook 78a in order to achieve a first dorsi-flexed position where the plantar fascia and Achilles tendon are slightly stretched for a given degree of tension. As the plantar fascia and Achilles tendon stretch from continued treatment, it is possible to adjust the device 10, by advancing element 50 progressively on hooks 78 until it is placed on hook 78e so as to place the foot in a more aggressively dorsi-flexed position, further stretching out the plantar fascia and Achilles tendon, as shown in FIG. 4, to achieve a lesser angle 104.

Preferably, device 10 is comfortably worn while the user is in a resting position such as while sleeping or sitting. It is also generally preferred that the user of the device be reasonably mobile, and able to walk easily without substantial hindrance or resistance to movement caused by device 10. In this manner, device 10 provides a highly comfortable, yet effective apparatus and method for treating plantar fasciitis.

Device 10 typically is formed of sufficiently lightweight materials that use at night will not keep the user awake or cause injury to others. Also, since only strap 90 is wrapped around the bottom of the foot in the vicinity of the arch, the user may still walk using device 10 without fear of slipping and falling or without fear of inadvertent injury due to kicking oneself or others.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims.

The present invention is directed to each individual feature, system, material and/or method described herein. In addition, any combination of two or more such features, systems, materials and/or methods, provided that such features, systems, materials and/or methods are not mutually inconsistent, is included within the scope of the present invention.

Various publications are cited herein, the disclosures of which are incorporated by reference in their entireties. In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

In the claims:

The invention claimed is:

1. A therapeutic device comprising:
   an upper portion constructed to be disposed adjacent a tibial bone of a lower leg;
   a foot portion constructed to be disposed adjacent a cuneiform bone of a foot, said foot portion being pivotally connected to said upper portion at a pivot point;
   a lower leg strap connected to said upper portion and constructed to be wrapped about the lower leg;
   a foot strap connected to said foot portion and constructed to be wrapped about a foot;
   an elastic tensioning element extending between spaced, confronting locations on said upper portion and said foot portion, said locations being spaced from said pivot point; and
   a plurality of spaced apart attachment points on a selected one of the upper portion and the foot portion, each of the plurality of attachment points being configured to selectively receive a first end of the elastic tensioning element to adjust tension in the tensioning element, wherein the first end of the elastic tensioning element is configured to be removably attached to a selected one of the plurality of spaced apart attachment points to provide a desired tension, and a second end of the elastic tensioning element is configured to be attached to the other of the upper portion and the foot portion.

2. The device of claim 1, wherein the lower leg strap is stretchable.

3. The device of claim 2, wherein the lower leg strap comprises a plurality of fabric hook and loop fasteners.

4. The device of claim 1, wherein the foot strap is stretchable.

5. The device of claim 4, wherein the foot strap comprises a plurality of fabric hook and loop fasteners.

6. The device of claim 1, wherein the attachment points comprise hooks.

7. The device of claim 6, wherein the first end of the elastic tensioning element includes a loop that is configured to extend through a feed hole and away from the pivot point, out an exit hole and back toward the pivot point to be looped over a selected one of the hooks.

8. The device of claim 1, wherein the upper portion is substantially rigid.

9. The device of claim 1, wherein the foot portion is substantially rigid.

10. The device of claim 1, wherein the foot portion includes a toe anchor to which the elastic tensioning element is attached.

11. The device of claim 1, wherein the pivot point includes a range of motion indicator.

12. The device of claim 1, wherein the elastic tensioning element comprises a shock cord.

13. The device of claim 1, wherein the elastic tensioning element comprises a single elastic cord.

14. The device of claim 1, wherein the plurality of spaced apart attachment points are on the upper portion.

15. A therapeutic device comprising:
an upper portion;
a foot portion pivotally connected to said upper portion at a pivot point;
a lower leg strap connected to said upper portion and constructed to be wrapped about a leg;
a foot strap connected to said foot portion and constructed to be wrapped about a foot;
a single looped shock cord extending between spaced, confronting locations on said upper portion and said foot portion, the locations being spaced from said pivot point; and
a plurality of spaced apart hooks on the upper portion, each of the plurality of hooks being configured to selectively receive a looped first end of the looped shock cord to adjust the tension in the cord, wherein the first end of the cord is configured to extend through a feed hole and upwardly along the upper portion, out an exit hole and downwardly along the upper portion to be looped over a selected one of the plurality hooks, and a second end of the cord is configured to attach to the foot portion.

16. The device of claim 15, wherein the upper portion is disposed adjacent a tibial bone.

17. The device of claim 15, wherein the foot portion is disposed adjacent a cuneiform bone.

18. The device of claim 15, wherein the pivot point includes a stop to limit an angle formed between the foot portion and the upper portion.

19. A method for treating plantar fasciitis comprising:
providing a splint device having an upper portion, a foot portion, an elastic tensioning element and a plurality of spaced apart attachment points on a selected one of the upper portion and the foot portion, each of the plurality of attachment points being configured to selectively receive a first end of the elastic tensioning element to adjust the tension in the tensioning element, the upper portion and foot portion being pivotally disposed with respect to one another at a pivot point;
detaching the elastic tensioning element from one of the upper portion and the foot portion;
pivoting the upper portion with respect to the foot portion;
securing the upper portion of the splint device to a lower leg adjacent a tibial bone;
securing the foot portion to an upper surface of a foot adjacent a cuneiform bone;
urging the foot portion and upper portion together with the elastic tensioning element which extends between the foot portion and the upper portion;
providing a desired tension on the elastic tensioning element by selecting a first one of the plurality of attachment points for securing the first end of the elastic tensioning element;
disengaging the tensioning element from the first one of the plurality of attachment points;
selecting another desired tension of the elastic tensioning element; and
re-attaching the elastic tensioning element to a second one of the plurality of attachment points that is spaced apart from the first one of the plurality of attachment points.

20. The method of claim 19, further comprising providing a range of motion indicator on the pivot point.

21. The method of claim 19, wherein securing the upper portion of the splint device to the lower leg comprises strapping the splint device to a calf region.

22. The method of claim 19, wherein securing the foot portion of the splint device to the upper surface of the foot comprises strapping the splint to a foot.

23. The method of claim 19 wherein the acts of providing a desired tension, disengaging the tensioning element, selecting another desired tension, and re-attaching the elastic tensioning element are performed for a fixed angle between the upper portion and the foot portion.

24. The method of claim 19 further comprising adjusting tension on the elastic tensioning element by adjusting an angle formed between the upper portion and the foot portion.

25. The method of claim 19, wherein the attachment points comprise hooks.

* * * * *